(12) United States Patent
McMillan

(10) Patent No.: US 7,656,517 B2  
(45) Date of Patent: Feb. 2, 2010

(54) TEST APPARATUS AND METHOD

(75) Inventor: Alison J. McMillan, Uttoxeter (GB)

(73) Assignee: Rolls-Royce plc, London (GB)

( * ) Notice: Subject to any disclaimer, the term of this patent is extended or adjusted under 35 U.S.C. 154(b) by 21 days.

(21) Appl. No.: 11/898,869

(22) Filed: Sep. 17, 2007

(65) Prior Publication Data

US 2008/0088824 A1    Apr. 17, 2008

(30) Foreign Application Priority Data

Oct. 12, 2006    (GB)    ................................. 0620193.3

(51) Int. Cl.
 *G01N 21/00*    (2006.01)
(52) U.S. Cl. .................................................. 356/237.1
(58) Field of Classification Search .... 356/237.1–241.6
 See application file for complete search history.

(56) References Cited

U.S. PATENT DOCUMENTS

| | | | | |
|---|---|---|---|---|
| 3,072,742 | A * | 1/1963 | Block | 348/770 |
| 3,333,103 | A * | 7/1967 | Barnes | 250/316.1 |
| 3,451,254 | A * | 6/1969 | Maley | 374/5 |
| 3,672,204 | A * | 6/1972 | Green | 374/43 |
| 3,758,233 | A * | 9/1973 | Cross et al. | 416/229 R |
| 4,639,188 | A * | 1/1987 | Swadley | 415/9 |
| 4,647,220 | A * | 3/1987 | Adams et al. | 374/5 |
| 4,664,470 | A * | 5/1987 | Yerazunis | 359/359 |
| 4,902,139 | A * | 2/1990 | Adiutori | 374/137 |
| 4,965,451 | A | 10/1990 | Sölter | |
| 5,310,312 | A * | 5/1994 | Balfour | 416/2 |
| 5,376,793 | A * | 12/1994 | Lesniak | 250/341.6 |
| 5,582,485 | A | 12/1996 | Lesniak | |
| 5,637,871 | A * | 6/1997 | Piety et al. | 250/330 |
| 5,953,161 | A * | 9/1999 | Troxell et al. | 359/618 |
| 6,367,968 | B1 * | 4/2002 | Ringermacher et al. | 374/7 |
| 6,703,631 | B2 * | 3/2004 | Suzuki | 250/504 R |
| 6,753,529 | B2 * | 6/2004 | DiMarzio et al. | 250/341.6 |
| 7,432,505 | B2 * | 10/2008 | Brummel | 250/332 |
| 2005/0207468 | A1 * | 9/2005 | McCullough et al. | 374/5 |

FOREIGN PATENT DOCUMENTS

WO    WO 98/05949    2/1998

* cited by examiner

*Primary Examiner*—Gregory J Toatley, Jr.
*Assistant Examiner*—Jarreas C Underwood
(74) *Attorney, Agent, or Firm*—Oliff & Berridge, PLC

(57) ABSTRACT

Previous testing of such test pieces as fan blades utilized in gas turbine engines has involved application of paint markings to identify fragments upon fragmentation of the test piece. Such fragmentation causes debris which will obscure paint markings and the paint itself may create clouds of dust obscuring visual images of the test piece under test conditions. By applying an image pattern comprising a number of lingering image patches, typically in the form of thermal patches upon the test components, and arranging the test components to be within an enclosure which is evacuated it will be appreciated that these image patterns linger and can be viewed by an appropriate monitor over a period at least of the test conditions. Utilization of extra visual spectrum radiation images extends the period when clear images of the test piece under test conditions can be seen and analyzed.

33 Claims, 1 Drawing Sheet

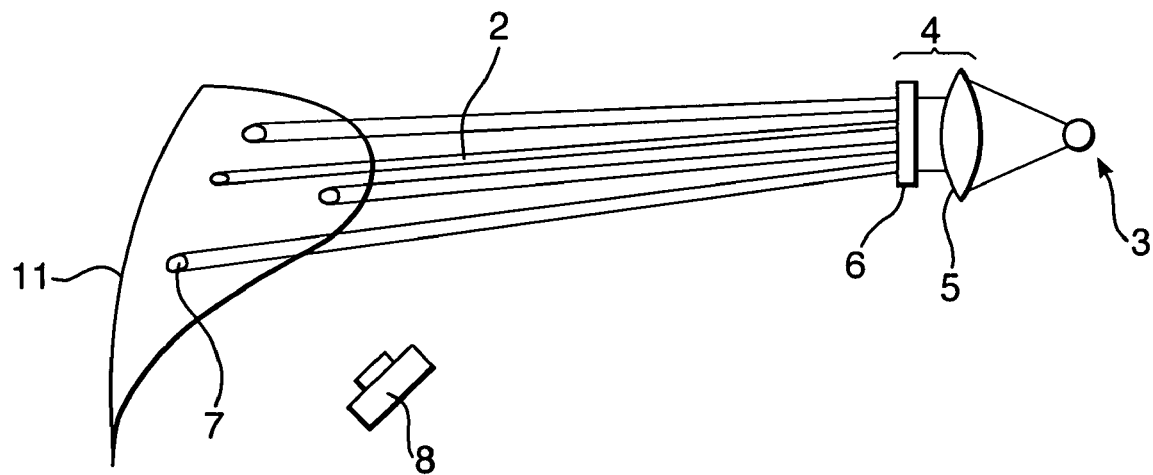
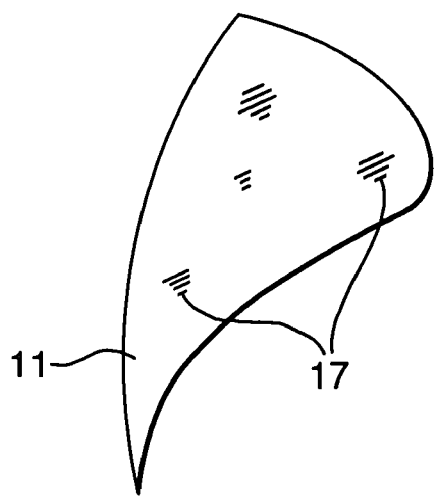
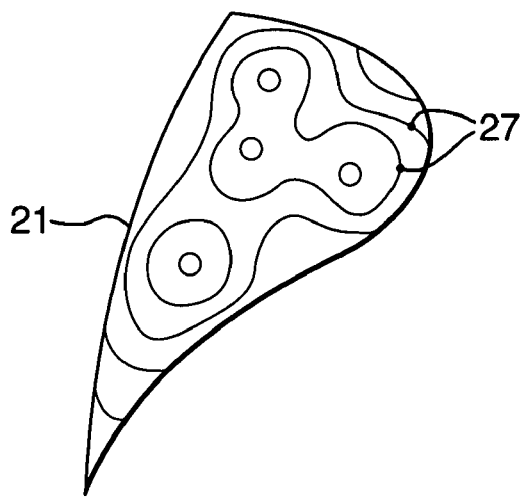

TEST APPARATUS AND METHOD

The present invention relates to test apparatus and methods for highlighting test pieces under test conditions such as blades used in gas turbine engines.

In order to ensure operational reliability it is known to test such components as blades within gas turbine engines in a number of operating environments and under test conditions. Particularly with regard to test pieces such as fan blades it will be understood that these blades are subject to percussive impacts such as with birds in operation and therefore the blades are tested to ensure that they react appropriately to such impacts and also should the blade disintegrate in service. Test conditions as indicated generally will include rotation and otherwise stressing the blade within an appropriate enclosure such as an evacuated spin pit.

The test piece will be monitored using cameras viewing the test piece or component, that is to say the fan blade, under test conditions. In order to reference and highlight the test piece it has been known to provide painted markings on the test piece which can be monitored by the camera as described.

Unfortunately paint markings on test pieces particularly after test are largely worn away and it is therefore difficult to identify the origin of various fragments from the test piece after the test conditions have been applied. It will be appreciated that it is advantageous to be able to reassemble the fragments of the test piece in order to validate predicted break up of the test pieces such as a blade in use. Generally, the test piece or fan blade as described will be arranged to fragment in a known manner and therefore validation of that property is important.

In view of the above, use of paint for component recognition under test conditions has a number of disadvantages including as described above the markings provided by the paint disappearing under test conditions as a result of wear. It will be appreciated that the paint may often not be very visible under test due to a number of multiple impacts creating a great deal of particulate dust and debris acting as a dense cloud obscuring camera based monitoring systems. Furthermore in order to achieve good visual images and in view of the necessary test conditions which may involve high speed rotation of the test piece it will be understood that high speed cameras are used which in turn will require intense light to meet exposure requirements. These lights will tend to be broken by test piece fragments further reducing visibility particularly after a couple of further rotations or otherwise.

Finally, it will also be appreciated that paint being frangible will tend to produce itself a cloud of fine particulate debris and matter, further adding to the density of clouding with regard to visual images.

In accordance with aspects of the present invention there is provided a method of highlighting a test piece, the method comprising selectively exposing a test piece to variable incident excitations to define separate image patches which linger upon a surface of the test piece, presenting the test piece to test conditions and taking extra visible light spectrum images of the test piece at least during such test conditions.

Typically, the image patches are provided as thermal patches upon the test piece. Generally, the incident excitation is provided by heating. Generally, the heating is provided by a heat radiation beam. Possibly, the heat radiation beam is presented as a pattern to provide the separable image patches. Possibly, the heating is provided by local inductive heating upon the test piece. Possibly, the incident excitations are pulsed. Possibly, the separable image patches are defined by emissivity or reflectivity differences in the surface of the test piece.

Generally, the separable image patches may be ameliorated to provide fringes of graduation as seen in the extra visible light spectrum image.

Generally, the method provides inhibition and/or isolation with regard to environmental incident excitation exchange with the test piece. Typically such isolation inhibits heat loss and/or gain by the test piece under test conditions where appropriate.

Possibly, the test conditions include rotation. Additionally, the test conditions may include inductive and/or percussive and/or other fragmentation of the test piece under test conditions.

Typically, the image patches are identifiable in the extra visible light spectrum images to facilitate tracking of the test piece fragments upon fragmentation.

Potentially, the test piece is located within a vacuum or partial vacuum.

Possibly, the method includes providing variable surface emissivity by physically altering the surface of the test piece. Possibly, such altering of the test piece includes provision of texturing and/or smoothing of the test piece as required.

Possibly, the test piece is painted with paint markings for visual identification under test conditions. Possibly, the paint markings provide at least some of the separable image patches upon the test piece.

Also in accordance with the present invention there is provided a test apparatus for testing test pieces, the apparatus comprising an enclosure and a mounting for a test piece, the apparatus including an extra visible light spectrum exciter to provide an image pattern upon a test piece in use comprising at least one image patch and each image patch visible upon the test piece when subject to test conditions as part of an extra visible light spectrum image.

Typically, the extra visible light spectrum exciter comprises a heater. Possibly, the image patch comprises a thermal patch or an ultraviolet patch upon the test piece.

Possibly, the enclosure inhibits and/or isolates the test piece from exchange of any environmental extra visible light spectrum excitation other than with regard to the extra visible light exciter in use as part of the apparatus.

Typically, the mounting provides means for providing test conditions for the test piece. Generally, the mounting allows rotation of the test piece. Possibly, the mounting allows induction and/or percussive and/or fragmentation of the test piece.

Possibly, the apparatus includes a monitor to view the test piece to provide extra visible spectrum light images of the image pattern upon the test piece in use. Typically, the monitor includes an infrared camera. Possibly, the monitor includes a visible light camera and/or Geiger counter.

Typically, the extra visible light spectrum exciter in the form of a heater comprises a radiant heat source to produce a heat beam. Possibly, the heat beam is focused by a focus element in use to define the image pattern upon the test piece in use. Typically, the focus element comprises a lens and diffraction grating. Possibly, the extra visible light spectrum exciter is pulsed. Possibly, the extra visible light spectrum exciter is inductive with regard to creating each image patch upon the test piece.

Embodiments of the present invention will now be described by way of example only with reference to the accompanying drawings, in which:

FIG. 1 is a schematic illustration of a test piece subject to testing in accordance with aspects of the present invention;

FIG. 2 is a schematic illustration of an alternative form of image patch pattern creation in accordance with aspects of the present invention; and FIG. 3 is a schematic illustration of an alternative image produced in accordance with aspects of the present invention.

As indicated above the inherent problem with regard to using normal visible images of a target test piece incorporating painted markings is that these markings may become obscured by debris and dust and wear off in use. Nevertheless, physically changing the test piece itself is not acceptable as the test piece will then not reflect the component in use. Aspects of the present invention provide for image patches which linger in a pattern upon a target test piece which are excited or are reflective or have an emissivity with regard to extra visible spectrum radiation such as infrared or ultraviolet. The embodiments described will be with regard to a blade utilised within a gas turbine engine and description will be principally with respect to thermal imaging creating infra-red images to be reviewed. However, as indicated other extra visual spectrum images may be provided by appropriate selective exposure or otherwise of a target test piece. In such circumstances a method and apparatus in accordance with the present invention provides a means of creating image patches upon the target test piece and utilisation of a monitor particularly in the form of a monitor to review infrared or ultraviolet cameras which may be utilised alongside existing visual spectrum cameras to provide a consolidation of images for analysis.

In accordance with aspects of the present invention, initially an enclosure in the form of a rig is assembled within which test pieces that is to say blades are located. The enclosure is partially or fully evacuated to facilitate operation. This partial or full evacuation may isolate or inhibit exchange between the blade and its environment in terms of heat loss or gain or excitation other than through use of an exciter in accordance with aspects of the present invention.

Once the blade is located within the rig enclosure in accordance with aspects of the present invention, image patches are created. Typically these image patches are created by the local heating and will linger not least due to the isolation of the test piece. Furthermore, these tests are high speed events so timescales for events are short in the order of a tenth of a second. There is significantly reduced convection because of the partial vacuum, with heat loss primarily through radiation or conduction, so that a hot patch will change temperature and shape in a predictable manner. Thus, electronic/computer imaging software will be used to interpret data at time t and match back to time=0, that is to say when the patch was created. FIG. 1 provides a schematic illustration of a test piece in the form of a blade 1 subject to an image pattern 2 generated by a radiant heat source 3 through a focusing mechanism 4 comprising a lens 5 and a diffraction grating 6. The pattern 2 incorporates a number of image patches 7 appropriately distributed about the target blade 1.

In the embodiment depicted in FIG. 1 it will be appreciated that the heating of the blade 1 is generally remote using the source 3. However, as an alternative it will also be understood that localised inductive heating may be provided by use of an appropriate excitation radiation focused upon the target at particular patches 7 to create temporary differentials across the blade 1. By providing heating to patches 7 it will be appreciated that these patches 7 create different areas having different temperatures and shaping in an approximate pattern identifiable in an image viewed by a monitor 8. In such circumstances the monitor 8 through use of extra visible radiation responses readily identifies the pattern upon the target test piece 1 which can be distinguished in use. Different patterns can be applied to different target components and blades or for different regions of a single target component or blade and identified by the monitor 8 during test conditions.

As indicated above these test conditions may include rotation of the blade 1 in association with other blades or destruction of the blade 1 through percussive impacts or otherwise. The monitor 8 therefore can collect a number of images as the blade 1 passes through these test conditions for later analysis. As the monitor 8 utilises extra visual spectrum radiation such as infrared or ultraviolet it will be understood that the monitor 8 is thus less dependent upon a clear view in the visible spectrum of the blade 1 and so debris clouds created from fragmentation of the component 1 can be more readily accommodated. It will be understood that debris clouds have ion effect at non visible wave lengths.

As an alternative to inducing or focusing heat upon the blade 1 to create local heating and therefore image patches 7 it may be possible in appropriate situations to utilise changes in surface emissivity within the blade 1 itself or to provide specific creation of such variations in emissivity in the blade 1 through roughing and smoothing to again create image patches which can be discernible by the monitor 8.

Again using heating excitation means for generating image patches it will be appreciated that the heat in the blade 1 will disperse through conduction and radiation but not via convection when the component blade 1 is located within an evacuated enclosure. In such circumstances the local heating pattern as initially generated by the patches 7 will linger but gradually change over time but this can be predictable and matched or simply observed during the test. It will also be understood that the patches 7 can be regularly "refreshed" as the blade 1 passes by pulsing the pattern to coincide with the blade as it passes through the stream of that pattern 2.

With regard to image pattern dispersion with respect to the patches 7 it will also be understood that blades and other test components may be made from a number of materials, some of which have high thermal conductivity and others which have low thermal conductivity and in some cases there will be orthotropy, that is to say thermal conductivities in different material directions. These changes in the image pattern viewed by the monitor 8 as indicated can be predicted or observed during test condition phases with respect to the blade 1 and therefore utilised with respect to analysis of the blade or other test piece under test conditions.

When a test is initiated as indicated a fixed programme of test conditions will be applied to that test piece and in accordance with certain test conditions the test piece will be tested until destruction and fragmentation of the test piece. In such circumstances even though the image pattern is changing this will generally be a slow process compared to the length of time under extreme test conditions.

A particular situation of concern is with regard to a so called fan blade off where one blade is released and its effect upon the remaining blades in a fan blade assembly is considered. Typically, the blade 1 under test conditions is generally released by an explosive fracture and then the action of the released blade upon the other blades in the assembly subject to a high rotation speed is considered. In such circumstances as indicated above it is the rotations after blade off which will be monitored by the monitor 8 and in such circumstances changes in the image pattern may be minimal. Nevertheless, where there is a more substantial period between the presentation of the image pattern and performance of the test conditions, that is to say start up time to reaching a desired speed, this significant period of time can be accommodated by refreshing the image pattern as described above.

If the start up time is too long for thermal patch marking to be useful an alternative is to mark the component during fan speed run up. This marking can be achieved through focusing the radiant heat as described above and through strobe pulsing, that is to say one heating pulse sequence per rotation cycle. A particular pattern can be applied to the blade as required. Alternatively, the heating beam assembly to create the pattern itself may be rotated in synchronisation with the target test piece or blade 1.

With thermal image patches it will be understood infrared cameras are utilised in the monitor to obtain images during test conditions. These infrared cameras will be able to identify individual test pieces and portions of test pieces by the image pattern created upon those test pieces and through utilisation of temperature differentials across the test piece. It will be appreciated that test pieces such as fan blades are relatively large and therefore appropriately spaced image patches can be created for distinct patterns across each test component in an assembly. Thus, even though these image patterns will change with time and/or heat diffusion it will be understood that impact debris in particular which has previously obscured visual spectrum pictures will have less or little impact upon the infrared images taken of the image patches in the form of thermal patches or zones in a distinct pattern upon the test component.

In addition to the advantages with regard to infrared cameras being able to identify thermal image patches in a pattern for identification through the test conditions it will also be understood that infrared cameras will also be able to pick up additional local heating as a result of component impacts. Although current cameras can identify flashes of light as indications of spin tip rubs, this information is of limited value. Infrared cameras give more details in terms of heating intensity for analysis and means of tracking individual broken off tip pieces can be achieved.

An additional feature of use of infrared cameras is the additional information provided by the images taken from such infrared cameras with regard to impact induced heating. It will be understood as described above in a fan blade assembly, a released blade will have impacts with trailing blades in the rotation direction. In such circumstances there is a distinct kinetic energy exchanged between the released blade and the trailing blades which can be monitored by the infrared camera. In short the impact induced heating patches are added to the initial image pattern created and the whole image can then be analysed. The underlying created image pattern thereby provides a reference for the blade position and condition whilst the induced heating caused by impacts gives a heat signature distinctive of that impact. Thus, predicted fragmentation and test piece response to test conditions can be compared with the images created such that the predictions can be adjusted in terms of practical test results.

It will be appreciated after the test conditions are removed from the test piece if the test piece has been fragmented then the thermal image data will be useful in terms of identifying where the respective fragmentation pieces are located. Typically, the rig enclosure will incorporate a pit within which the fragmentation pieces fall as a pile. Again as the enclosure is generally evacuated heat loss may be through conduction and radiation but not through convection thus within the evacuated pit the fragmentation pieces may still be identified by image patches retained at least for a short period of time after the fragmentation episode. In any event, the monitor in accordance with aspects of the present invention would be able to record the position of the fragmented pieces within the pit for subsequent retrieval.

Generally as indicated above image patches will be created by thermal action upon a test piece such as a blade component. Alternatively, as illustrated in FIG. 2, emissivity can be utilised in order to create image patches 17 again having a distinct pattern upon a test piece 11. The patches 17 may be created by roughening and smoothing within the surface of the test piece 11. These patches 17 created either by specific roughening and smoothing or through inherent differences in emissivity in the test piece 1 can be utilised as indicated above during test condition monitoring of the test piece 1 as seen by extra visual spectrum images through a monitor 8 (FIG. 1). It will also be understood that such roughening and smoothing will remain with the component fragments of the test piece 1 after the test conditions and so if the test piece 11 has fragmented may be utilised for reassembling the pieces.

By applying an image pattern created by emissivity differences it will be understood that the images taken may not be simply thermal or excited image patches created upon the test piece 1 but also may include visually identifiable patches. These visible and/or emissivity patches may also be created by painted or other marking regimes upon the test piece 1. In such circumstances rather than provide a focused heat source to create the patches as described above, it will be understood that a de-focussed heat could stimulate emissivity patches on the whole test piece. Test components may be identified in accordance with aspects of the invention depicted in FIG. 2 through differences in how the patches 17 reflect incoming infrared radiation, that is to say a diffuse or whole component heat source. Such an approach is called albedo in which emissivity is given by the relationship $A=1-\epsilon$ where $A$=total scattered power over incident power and $\epsilon$=emissivity. As depicted in FIG. 3 fringes 27 can be created in a pattern identifiable in a monitor of temperature differences in a test piece 21. The emissivity pattern given by the fringes 27 is analysed by appropriate consideration of the infrared image received by the monitor such that by appropriate choice sensitivity to small angular differences in the fringes 27 can be utilised to detect vibration and possibly shock waves within the test piece 1 under test conditions. It will be appreciated that such analysis with respect to vibration shock waves is further rendered possible through necessary use of high camera speeds in view of the high rotational speeds of components such as blades as test pieces in accordance with aspects of the present invention. In such circumstances a high number of images will be taken which can be compared sequentially for differences in the albedo fringes of temperature differences across the test piece 1 for analysis.

Ideally methods and apparatus in accordance with aspects of the present invention will combine both visual spectrum and extra visual spectrum radiation images for appropriate analysis. In such circumstances apparatus and methods will utilise a number of cameras for different visual spectrum and extra visual spectrum images with the full range of images utilised for appropriate consolidated analysis. It will be appreciated that previous visual spectrum images have been analysed by highly skilled test condition specialists in order to review film footage of the visual images or analysis. These specialists have acquired through experience knowledge of component responses under test conditions such that the inherent degradation in film quality towards the end of test conditions, that is to say after fragmentation of the test piece when visibility is poor due to small particle debris clouds can be supplemented by projection of previous experiences. Inherently, human interpretation has its own limitations such that by providing in accordance with aspects of the present invention image patterns in the form of image patches upon test components which can be seen through by extra visual spectrum image cameras and monitors it will be understood that the component through the test conditions can be monitored in a reference frame given by the distinct image patches. Furthermore, through appropriate image consolidation through the reference of the patches in the images of the components, a three dimensional image of the test component under analysis can be resolved.

In view of the above, it will be appreciated that aspects of the present invention allow more extended analysis of test pieces under test conditions by extending the period when practical imagery with regard to the test piece can be seen. Previous purely visual imagery as indicated utilised paint markings which may wear off or become obscured by debris clouding. This visual imagery may be supplemented by the present extra visual spectrum images as a combination to identify test piece performance under test conditions. Furthermore, if the paint markings have been removed after test conditions such as fragmentation have occurred the thermal or other image patterning in accordance with the present invention may linger at least for a period of time to allow automated image capture of the fragments in the pit of the test apparatus in accordance with aspects of the present invention such that their location is marked for subsequent recovery.

As indicated above generally it is preferred to utilise both visual spectrum images as well as extra visual spectrum images to provide a fuller picture with respect to analysis of test pieces. By use of aspects of the present invention it will be understood that the number of paint markings used may reduce which in turn will reduce dust created by such paint as a result of the test conditions as well as the necessity for intense lighting to enable such visual paint markings to be viewed in the visual images for an extended period of time.

Although described with regard to infrared heat image patches in accordance with aspects of the present invention it will also be appreciated that ultraviolet illumination and ultraviolet image capture may be utilised to give an even wider frequency spectrum which can be seen through the dust clouds created by test piece fragmentation and paint dissipation in accordance with test conditions upon test components such as fan blades.

In addition to testing fan blades utilised in gas turbine engines it will also be appreciated that ballistic test conditions with regard to other components under fragmentation or other test conditions may be analysed in accordance with aspects of the present invention.

The invention claimed is:

1. A method of testing a test piece, the method comprising:
   selectively exposing a test piece to variable incident excitations to define separate image patches which linger in use upon a surface of the test piece,
   presenting the test piece to test conditions, the test conditions including fragmentation of the test piece, and
   taking extra visible light spectrum images of the test piece at least during such test conditions.

2. The method of claim 1 wherein the image patches are provided as thermal patches upon the test piece.

3. The method of claim 1 wherein the incident excitation is provided by heating.

4. The method of claim 3 wherein the heating is provided by a heat radiation beam.

5. The method of claim 4 wherein the heat radiation beam is presented as a pattern to provide the separable image patches.

6. The method of claim 3 wherein the heating is provided by local inductive heating upon the test piece.

7. The method of claim 1 wherein the incident excitations are pulsed.

8. The method of claim 1 wherein the separable image patches are defined by emissivity or reflectivity differences in the surface of the test piece.

9. The method of claim 1 wherein the separable image patches are ameliorated to provide fringes of graduation as seen in the extra visible light spectrum images.

10. The method of claim 1 wherein the method provides inhibition and/or isolation with regard to environmental incident excitation exchange with the test piece.

11. The method of claim 10 wherein such isolation inhibits heat loss and/or gain by the test piece under test conditions where appropriate.

12. The method of claim 1 wherein the test conditions include rotation.

13. The method of claim 1 wherein the image patches are identifiable in the extra visible light spectrum images to facilitate tracking of the test piece fragments upon fragmentation.

14. The method of claim 1 wherein the test piece is located within a vacuum or partial vacuum.

15. The method of claim 1 wherein the method includes providing variable surface emissivity by physically altering the surface of the test piece.

16. The method of claim 15 wherein such altering of the test piece includes provision of texturing and/or smoothing of the test piece as required.

17. The method of claim 1 wherein the test piece is painted with paint markings for visual identification under test conditions.

18. The method of claim 17 wherein the paint markings provides at least some of the separable image patches upon the test piece.

19. A test apparatus for testing test pieces, the apparatus comprising:
   an enclosure and a mounting for a test piece, and
   an extra visible light spectrum exciter to provide an image pattern upon a test piece in use comprising at least one image patch and each image patch visible upon the test piece when subject to test conditions as part of an extra visible light spectrum image, the test conditions including fragmentation of the test piece.

20. The apparatus of claim 19 wherein the extra visible light spectrum exciter comprises a heater.

21. The apparatus of claim 19 wherein the image patch comprises a thermal patch or an ultraviolet patch upon the test piece.

22. The apparatus of claim 19 wherein the enclosure inhibits and/or isolates the test piece from exchange of any environmental extra visible light spectrum excitation other than with regard to the extra visible light exciter in use as part of the apparatus.

23. The apparatus of claim 19 wherein the mounting provides means for providing test conditions for the test piece.

24. The apparatus of claim 19 wherein the mounting allows rotation of the test piece.

25. The apparatus of claim 19 wherein the apparatus includes a monitor to view the test piece to provide extra visible spectrum light images of the image pattern upon the test piece in use.

26. The apparatus of claim 25 wherein the monitor includes an infrared camera.

27. The apparatus of claim 25 wherein the monitor includes a visible light camera and/or Geiger counter.

28. The apparatus of claim 21 wherein the extra visible light spectrum exciter in the form of a heater comprises a radiant heat source to produce a heat beam.

29. The apparatus of claim 28 wherein the heat beam is focused by a focus element in use to define the image pattern upon the test piece in use.

30. The apparatus of claim 19 wherein the extra visible light spectrum exciter is pulsed.

31. The apparatus of claim 19 wherein the extra visible light spectrum exciter is inductive with regard to creating each image patch upon the test piece.

32. An apparatus for testing test pieces operated in accordance with the method of claim 1.

33. The apparatus of claim 30 wherein the focus element comprises a lens and diffraction grating.

* * * * *